United States Patent [19]

French et al.

[11] Patent Number: 4,957,658

[45] Date of Patent: Sep. 18, 1990

[54] PROCESS AND COMPOSITION FOR PROVIDING REDUCED DISCOLORATION CAUSED BY THE PRESENCE OF PYRITHIONE AND FERRIC ION IN WATER-BASED PAINTS AND PAINT BASES

[75] Inventors: Cheryl B. French, Glastonbury; Sigmund Breister, Hamden, both of Conn.

[73] Assignee: Olin Corporation, Cheshire, Conn.

[21] Appl. No.: 315,629

[22] Filed: Feb. 24, 1989

Related U.S. Application Data

[63] Continuation-in-part of Ser. No. 91,684, Aug. 31, 1987, Pat. No. 4,818,436.

[51] Int. Cl.$^5$ .................... G09K 15/32; C08K 5/36; C07C 143/90
[52] U.S. Cl. .............................. 252/400.23; 524/131
[58] Field of Search ..................... 252/400.23; 524/131

[56] References Cited

U.S. PATENT DOCUMENTS

| | | | |
|---|---|---|---|
| 2,809,971 | 11/1957 | Bernstein et al. | 524/298 |
| 3,159,640 | 12/1974 | McClure et al. | 526/290 |
| 3,899,293 | 8/1975 | Bush | 422/15 |
| 4,169,086 | 9/1979 | Nolken | 524/131 |
| 4,533,736 | 8/1985 | Trotz et al. | 546/290 |
| 4,557,896 | 12/1985 | Brocklebank et al. | 422/14 |
| 4,774,303 | 9/1988 | Denzinger et al. | 526/317.1 |
| 4,818,436 | 4/1989 | French et al. | 252/400.23 |

FOREIGN PATENT DOCUMENTS 0077630 10/1981 European Pat. Off. .
2262375 6/1974 Fed. Rep. of Germany .

OTHER PUBLICATIONS

"DEQUEST ® 2010 Phosphonate for Scale and Corrosion Control, Chelation, Dispersion", Technical Bulletin No. IC/SCS-323, Monsanto Industrial Chemicals Co., St. Louis, Mo.

Chemical Abstracts, vol. 73, 1970, Abstract 37188a, Jacques.

*Primary Examiner*—Nathan M. Nutter
*Attorney, Agent, or Firm*—Dale Lynn Carlson

[57] ABSTRACT

This invention relates generally to paints and paint bases and, more specifically, to a process and composition for providing reduced discoloration of paints and paint bases containing a pyrithione and ferric ion.

9 Claims, No Drawings

PROCESS AND COMPOSITION FOR PROVIDING REDUCED DISCOLORATION CAUSED BY THE PRESENCE OF PYRITHIONE AND FERRIC ION IN WATER-BASED PAINTS AND PAINT BASES

This is a continuation-in-part application of U.S. patent application Ser. No. 091,684, filed Aug. 31, 1987, now U.S. Pat. No. 4,818,436.

This invention relates generally to paints and paint bases and, more specifically, to a process and composition for providing reduced discoloration of paints and paint bases containing a pyrithione and ferric ion.

Sodium pyrithione [also called the sodium salt of 1-hydroxy-2-pyridinethione, sodium pyridine-2-thiol-N-oxide, or 2-pyridinethiol-1-oxide, Na salt] is typically employed as a biocide and preservative in functional fluids, such as metalworking fluids, lubricants, cosmetics and toiletries.

Likewise, zinc pyrithione [also known as zinc pyridine-2-thiol-N-oxide or bis[1-hydroxy-2(H)pyridinethionato]-zinc] is an excellent biocide. It has been employed as a broad-spectrum anti-microbial agent and preservative in metalworking fluids, plastics, and cosmetics. Its principal uses are as an anti-dandruff agent in hair products or as a preservative in various cosmetics and toiletries.

Since the aesthetics of metalworking fluids, cosmetics and toiletries normally require certain desirable colors, and the formulators of such products go to great lengths to achieve specific color effects, any ingredient which causes the functional fluid to vary much from white or colorless may make the colorant formulators' task very difficult.

In the presence of ferric ion, sodium or zinc pyrithione-containing compositions tend to turn blue even though the ferric ion is present in mere trace amounts. This blue discoloration is undesirable for aesthetic reasons.

In addition to the aesthetics problems, the blue coloration problem associated with the presence of ferric ion causes a functioning problem in the pyrithione-containing compositions. This problem results from the fact that the pyrithione tends to form a blue precipitate in the presence of ferric ion. The precipitate reduces the amount of available pyrithione throughout the composition, thereby diminishing the biocidal protection thereof.

Yet another problem caused by the blue discoloration is encountered when attempting to utilize pyrithione as an antimicrobial agent in fully-formulated water-based paints and so-called "paint bases" (i.e., the partially-formulated paint before pigment addition). The discoloration adversely affects the desired color, producing an off-color product. Possibly for this reason, pyrithione has not been used heretofore in paints or paint bases to the knowledge of the present inventors.

A solution to this blue discoloration problem in paints and paint bases which enables pyrithione to be utilized therein would be highly desired by the paint manufacturing community.

In one aspect, the present invention relates to a process for reducing or inhibiting the formation of a blue discoloration in a water-based paint or paint base composition caused by the presence of ferric ion and sodium or zinc pyrithione in the composition which comprises adding thereto an alkali metal or alkaline earth metal salt of 1-hydroxyethane-1,1-diphosphonic acid (also referred to herein as "HEDP").

In another aspect, the present invention relates to a water-based paint or paint base composition free of, or inhibited against, blue discoloration otherwise caused by the presence of ferric ion and sodium or zinc pyrithione therein comprising an aqueous sodium or zinc pyrithione and an alkali metal or alkaline earth metal salt of 1-hydroxyethane-1,1-diphosphonic acid.

The sodium pyrithione employed in the process and composition of the present invention is a well-known commercial product and is commonly made by reacting 2-chloropyridine-N-oxide with NaSH and NaOH. See U.S. Pat. No. 3,159,640, which issued to McClure on Dec. 1, 1964, the disclosure of which is incorporated herein by reference in its entirety.

Zinc pyrithione may be made by reacting 1-hydroxy-2-pyridinethione or a soluble salt thereof with a zinc salt (e.g., $ZnSO_4$) to form a zinc pyrithione precipitate. See U.S. Pat. No. 2,809,971, which issued to Bernstein and Losee on Oct. 15, 1957, incorporated herein by reference.

A wide variety of alkali metal and alkaline earth metal salts of HEDP are useful within the scope of the present invention such as, for example, the sodium, potassium, calcium and magnesium salts of HEDP. Of these, sodium and potassium are preferred. The most preferred salt is potassium based upon its ease of preparation by reacting HEDP with KOH (while cooling the reaction mixture) within a pH range of between about 11 and about 13, more preferably between about 11 and about 12. Below a pH of about 11, precipitation of the HEDP-$K_4$ and/or the pyrithione is frequently encountered, whereas a pH of above about 13 tends to cause pyrithione stability problems upon aging of the composition.

In contrast to the ease of preparation of the potassium salt, the sodium salt of HEDP generally requires maintaining the temperature at an elevated level of as high as 90° C. or higher and a pH of between about 10.5 and about 13, preferably between about 11.5 and about 12. Lower temperatures can result in the heavy precipitation of the hydrated trisodium salt of HEDP during the preparation.

In water-based paints and paint bases, a level of ferric ion of 10 ppm or higher is not uncommon. By incorporating an effective amount of the metal salt of HEDP into the composition, the blue coloration attributable to the presence of ferric ion bound with pyrithione is suitably reduced, eliminated, or avoided.

The amount of the above-specified metal salt of HEDP incorporated into the compositions of the present invention can vary over a wide range. If the preferred HEDP-$K_4$ salt is used, the amount of HEDP-$K_4$ is desirably between about 33 and about 75 weight percent based on the total weight of HEDP-$K_4$ and pyrithione in the composition. The upper limit on HEDP-$K_4$ in this range of ratios provides an adequate amount of HEDP-$K_4$ if the total amount of ferric ion in the composition is no greater than about 150 ppm. If larger quantities of ferric ion are expected to be encountered, the amount of HEDP-$K_4$ is increased accordingly.

Thus, if the composition is pre-determined to have a very high ferric ion content, the HEDP-$K_4$ level can be adjusted accordingly to a higher level as is required to achieve the objective of reduced blue coloration. If significant amounts of calcium or magnesium ions are expected to be present or in the paint or paint base (e.g., caused by the use of hard water by the manufacturer in the production of the paint or paint base), a chelator such as ethylenediamine tetraacetic acid (EDTA) is suitably utilized in an amount of between 50 and 500 ppm or higher in the paint or paint base, as needed to chelate the calcium or magnesium ions.

Without wishing to be bound by any particular theory, the efficacy of the HEDP-$K_4$ in preventing or reducing blue coloration in the compositions of the present invention is believed by the present inventors to be attributable to the superior ferric ion binding capability of the above-specified metal salts of HEDP, as compared to the ferric ion binding ability of the pyrithione in the composition. More specifically, since the blue coloration is believed by the instant inventors to be caused by ferric ion bound to pyritione, blue color elimination or prevention is believed to be effected in accordance with this invention by virtue of the superior ion-binding capability of HEDP-$K_4$ in competition with the pyrithione present in the composition.

Indeed, some compositions within the scope of the present invention exhibit an initial bluish coloration upon addition of ferric ion. Upon standing for a few minutes, the blue color disappears indicating the effectiveness of ferric ion binding by HEDP-$K_4$ upon equilibration.

The term "discoloration" as employed herein with respect to pyrithione-containing compositions may mean any unacceptable gray, blue, black, purple or color other than the natural color or desired artificial color of the paint or paint base formulation. It is noted that the natural color of a sodium pyrithione itself is a clear yellow. One way of quantifying the discoloration is by measuring the Hunter color parameters and calculating a whiteness value from them. Another method is to visually inspect the composition for any signs of off-whiteness, as compared to the desired or white color.

The following examples are intended to illustrate, but in no way limit the scope of, the present invention.

EXAMPLE 1

Efficacy of HEDP-$K_4$ in Eliminating Blue Coloration Caused by The Presence of Ferric Ion in Sodium Pyrithione-Containing Paint Bases In order to test the effectiveness of HEDP-$K_4$ in eliminating or reducing blue color caused by ferric ion in six pyrithione-containing paint bases, the following experiments were conducted.

Six samples weighing 150 grams each of six different brands of aqueous (latex) paint tint bases (purchased "off-the-shelf") were placed in paper cups. A birch tongue depressor was then dipped into each sample and then allowed to dry to provide a control or "blank" comparison. Forty percent aqueous sodium pyrithione was added to each sample to provide a sodium pyrithione level of 53.3 ppm in each sample. Ferric chloride was then added to each sample to provide a concentration of 64 ppm of ferric ion in each sample. Tongue depressor coatings were taken to provide comparison. Finally, one milliliter aliquots of an aqueous mixture of HEDP-$K_4$ and EDTA-$Na_4$ were added to each sample, and tongue depressor coating samples therein.

The HEDP-$K_4$ was prepared as follows:

A 60 weight percent aqueous HEDP acid solution was added to a reaction vessel in an amount of 40.2 weight percent based on the weight of this acid plus KOH to be added. The reaction vessel was adequately cooled with an ice bath. Fifty weight percent aqueous KOH in an amount of 59.8 percent by weight based upon the total weight of HEDP plus KOH was added slowly to the reaction vessel containing the HEDP slowly until the pH of neutralization was 12.0. The resulting HEDP-$K_4$ was then mixed with EDTA-$Na_4$ to make the aqueous mixture utilized as described in the previous paragraph.

The samples were subjected to colorimeter tests to measure the extent of discoloration of each paint base before and after the aqueous mixture of HEDP-$K_4$ and EDTA-$Na_4$ was added to the samples. Color values were obtained using a SPECTROGARD color system obtained from Pacific Scientific Corporation. The results are presented in Table I below.

TABLE I

Paint Base Discoloration Measurements[1] Before and After HEDP-$K_4$ and EDTA-$Na_4$ Addition[2]

| Paint Base Sample No. | Before Addition | After Addition |
| --- | --- | --- |
| 1 | −4.33 | −2.71 |
| 2 | −4.45 | +0.24 |
| 3 | −3.90 | −0.52 |
| 4 | −3.95 | +1.61 |
| 5 | −4.49 | −1.58 |
| 6 | −4.24 | −1.35 |

[1]The measurements represent the difference in the "L" values ("whiteness" values) between the blank and the corresponding sample containing HEDP-$K_4$/EDTA-$Na_4$ and ferric ion. The measurements were visually displayed as DELTA values on the SPECTROGARD display monitor. A positive number designates a lighter color than the blank and a negative number designates a darker color than the blank.
[2]The additions of HEDP-$K_4$ plus EDTA-$Na_4$ to each paint base was from an aqueous mixture containing 3176.7 ppm of HEDP-$K_4$ (equal to 1815.2 ppm of HEDP acid) and 737.3 ppm of EDTA-$Na_4$.

The results as given in Table I above show that in the addition of the HEDP-$K_4$ plus EDTA-$Na_4$ to each paint base significantly reduced the discoloration caused by ferric ion together with sodium pyrithione. Indeed, for Samples 2 and 3, the color achieved after the HEDP-$K_4$ plus EDTA-$Na_4$ addition was virtually identical to the corresponding blank samples (without ferric ion) as can be seen from the near zero Hunter color values of +0.24 and −0.52, respectively.

EXAMPLE 2 (Proposed Example)

Efficacy of HEDP-$K_4$ in Eliminating Blue Coloration Caused by the Presence of Ferric Ion in Zinc Pyrithione-Containing Paint In the presence of ferric ion, zinc pyrithione-containing paint compositions also tend to turn blue to grey, although at a much slower rate than do the sodium pyrithione-containing paints.

48 Percent aqueous zinc pyrithione is added to a white paint sample to provide a level of 40.0 ppm of zinc pyrithione in the sample. Ferric chloride is then added to provide a concentration of 64 ppm of ferric ion in the sample. Upon standing for a month, the paint is found to turn bluish in color. Finally, 42 percent active HEDP-$K_4$ is added to the paint sample to provide a level of 1330 ppm. The color of the paint returns to white. Colorimeter measurement is made on the sample before and after addition of each ingredient to document the color changes.

What is claimed is:

1. A process for reducing or inhibiting the formation of a blue discoloration in a water-based coating composition caused by the presence of ferric ion and sodium or zinc pyrithione in the composition which comprises adding thereto an alkali metal or alkaline earth metal salt of 1-hydroxyethane-1,1-diphosphonic acid.

2. The process of claim 1 which additionally comprises adding to said coating composition composition an alkali metal salt of ethylene diamine tetraacetic acid.

3. The process of claim 1 wherein said alkali metal or alkaline earth metal salt of 1-hydroxyethane-1,1-diphosphonic acid is selected from the group consisting of the sodium, potassium, calcium, and magnesium salts of 1-hydroxyethane-1,1-diphosphonic acid, and mixtures thereof.

4. The process of claim 1 wherein the amount of said alkali metal or alkaline earth metal salt of 1-hydroxyethane-1,1-diphosphonic acid is between about 33 and about 75 weight percent based upon the total weight of said alkali metal or alkaline earth metal salt of 1-hydroxyethane-1,1-diphosphonic acid plus said sodium pyrithione.

5. A water-based coating composition composition free of, or inhibited against, blue discoloration otherwise caused by the presence of ferric ion and sodium or zinc pyrithione therein comprising an aqueous sodium pyrithione and an alkali metal or alkaline earth metal salt of 1-hydroxyethane-1,1-diphosphonic acid.

6. The composition of claim 5 which additionally contains an alkali metal salt of ethylenediamine tetraacetic acid.

7. The composition of claim 5 wherein said alkali metal or alkaline earth metal salt of 1-hydroxyethane-1,1-diphosphonic acid is selected from the group consisting of the sodium, potassium, calcium, and magnesium salts of 1-hydroxyethane-1,1-diphosphonic acid, and mixtures thereof.

8. The composition of claim 5 wherein the amount of said alkali metal or alkaline earth metal salt of 1-hydroxyethane-1,1-diphosphonic acid is between about 33 and about 75 weight percent based upon the total weight of said alkali metal or alkaline earth metal salt of 1-hydroxyethane-1,1-diphosphonic acid plus said sodium pyrithione.

9. The composition of claim 6 wherein said alkali metal salt of ethylenediamine tetraacetic acid is present in an amount of between 50 and 500 ppm based upon the total weight of the composition.

* * * * *